United States Patent [19]

Aysta et al.

[11] Patent Number: 5,019,084

[45] Date of Patent: May 28, 1991

[54] CORNEAL HOLDER

[75] Inventors: James E. Aysta, Stillwater; Richard L. Lindstrom, Wayzata; Debra L. Skelnik, Cambridge, all of Minn.

[73] Assignee: Minnesota Mining and Manufacturing Company, St. Paul, Minn.

[21] Appl. No.: 893,785

[22] Filed: Aug. 6, 1986

[51] Int. Cl.⁵ .................. A61B 17/32; A45C 11/04
[52] U.S. Cl. .................................... 606/107; 206/5.1
[58] Field of Search .................. 128/305, 305.1, 310; 206/5.1; 623/4, 5; 606/107, 167

[56] References Cited

U.S. PATENT DOCUMENTS

| | | |
|---|---|---|
| 2,929,603 | 3/1960 | Stewart . |
| 3,058,471 | 10/1962 | Shope . |
| 3,115,146 | 12/1963 | Erwin .................................. 206/5.1 |
| 4,077,411 | 3/1978 | Ward .................................. 128/305 |
| 4,077,411 | 3/1978 | Ward . |
| 4,205,747 | 6/1980 | Gilliam et al. ...................... 206/5.1 |
| 4,236,519 | 12/1980 | La Russa et al. .................. 128/305 |
| 4,257,521 | 3/1981 | Poler .................................. 206/5.1 |
| 4,423,809 | 1/1984 | Mazzocco ........................... 206/5.1 |

OTHER PUBLICATIONS

"Tissue Processing", by M. A. Gallagher, pp. XI-1 through XI-4, in *Eye Bank Technician Manual*, Eye Bank Association of America, Houston, TX, 1984.

B. F. Boyd, Highlights of Ophthamology Letter, vol. XIV(2): 1-16 (1986).

"Wide Field Specular Microscopy of Excised Donor Corneas", C. W. Roberts et al., Arch. Ophthalmol. 99: 881-883 (1981).

"Corneal Holder", Amer. J. Ophthalmol. 80(3) Part II: 551-552 (1975).

Kiely et al., "Meridional Variations of Corneal Shape", Amer. J. Optom. Physiol. Optics, 61(10): 619-626, 1984.

"Minnesota System Corneal Preservation", Lindstrom et al., Brit. J. Ophthalmol., 70: 47-54, 1986.

"Examination and Photography of Donor Corneal Endothelium", W. M. Bourne, Arch. Ophthalmol. 94: 1799-1800 (1976).

"A New Punch for Corneal Transplantation", D. M. Lieberman, Amer. J. Ophthalmol. 83: 419-420 (1977).

"Products for Ophthalmology"—PRO CSVC ™ (Corneal Storage and Viewing Chamber).

*Primary Examiner*—C. Fred Rosenbaum
*Attorney, Agent, or Firm*—Gary L. Griswold; Walter N. Kirn; Philip M. Goldman

[57] ABSTRACT

A corneal holder, amenable for use in both a corneal storage system and a corneal cutting system with minimal physical manipulation of the corneal tissue itself. The holder provides a passageway through the apertures of both a base member and a cap member that is configured to allow a cutting device to be passed into cutting contact with a predetermined portion of the corneal tissue. The holder allows radial orientation of the predetermined portion in order to limit astigmatism; as well as constriction of the periphery of the corneal tissue during storage in order to alleviate swelling of the tissue due to fluid absorption.

9 Claims, 1 Drawing Sheet

CORNEAL HOLDER

FIELD OF THE INVENTION

The present invention relates to procedures and means for physically handling corneal tissue that has been obtained from a donor eye, in order to perform such functions as storing, transporting, microscopically evaluating, and cutting the tissue in a manner that provides a portion of the corneal tissue that is suitable for implantation in a recipient eye.

BACKGROUND ART

For purposes of possible transplantation to a recipient eye, the cornea from a donor eye is typically excised as a generally circular section of tissue that includes a small outer rim of scleral tissue.

This corneal tissue is then generally subjected to a variety of physical manipulations and procedures, including storage, transport, microscopic evaluation and lastly, "trephining" a procedure in which a circular plug, i.e., "donor button", of the desired size is cut out from the desired location for use as an transplant.

An excision and storage technique commonly used in many eye banks is outlined in the chapter entitled "Tissue Processing", by M. A. Gallagher, pp. XI-1 through XI-4, in *Eye Bank Technician Manual,* Eye Bank Association of America, Houston, Tex., 1984. In this technique the corneal tissue is cut out, i.e., excised with small scissors in a generally circular shape having a 2-3 millimeter outer rim of scleral tissue. The tissue is typically transferred to a clear vial, and stored, free-floating, in sterile storage medium. Certain recent developments in the formulation of storage media purport to enable the storage of such explants for up to several days or even weeks, see, e.g., B. F. Boyd, Highlights of Ophthamology Letter, Vol. XIV(2): 1-16 (1986).

The corneal tissue is typically stored in the free-floating state until just before use when it is microscopically examined to evaluate the integrity of its endothelial surface, e.g., by removing the tissue with a forceps to a viewing chamber or viewing it directly in its storage vial as described, e.g., in "Wide Field Specular Microscopy of Excised Donor Corneas", C. W. Roberts et al, Arch. Ophthalmol. 99:881 $\propto$ 883 (1981). The condition and appearance of the endothelial and epithelial surfaces are critical factors to be determined in deciding whether a particular corneal tissue is suitable for implantation. Abrasions and loss of cells from the endothelial surface are major factors for rejecting many corneal tissues for use and can be attributed, at least in part, to damage done to the tissue during and by virtue of its storage.

In an adaptation of the free-floating storage system, Coopervision, Inc., Irvine, Calif. has a commercially available storage jar called a "PRO CSVC" which is described as a "Corneal Storage and Viewing Chamber" for use in conjunction with its microscope systems. The chamber consists essentially of two parts, i.e., a translucent plastic jar and a clear plastic cap.

The distinguishing feature of the jar is a circle formed by eight plastic spikes extending upwardly from the base of the jar, each being inwardly notched and then tapered downwardly at their tips so as to provide a support upon which corneal tissue can rest without falling between the spikes or into the open circle defined by their center.

The cap has a circular indented portion that is optically clear and configured to allow a microscope lens to penetrate the plane of the top of the cap a distance almost equal to the height of the cap, and to move about therein, in order to scan and focus on the corneal tissue when the tissue rests in the center of the chamber.

The cap indentation also serves to provide a barrier at the top of the jar chamber, thereby restricting the ability of the tissue to float out of its chamber. The tissue is nonetheless still free to move within the confines of the chamber, such that the jar might need to be tapped or swirled in an attempt to bring the tissue to rest in a centered position at the base of the chamber.

As with the free-floating storage vial described earlier, the tissue would of course, need to be physically grasped and removed from the chamber in order to place it carefully in a trephining device.

The basic trephining devices are simply cutting blocks and corneal punches. The tissue is carefully placed epithelial side down in a concave indentation in a block made out of a hard inert material such as Teflon, such that the center of the tissue is aligned with the center of the indentation, and the tissue rests in approximately its normal curvature during trephining. A circular metal trephine blade, attached to a punch mechanism, is then carefully aligned and oriented, in a manner analogous to a drill press, so as to hover above or lightly touch the tissue at the desired, generally central, location. The blade is then tapped or turned down into the tissue with sufficient force and to a sufficient distance to cut out a plug.

Devices have been described for securely holding corneal tissues during trephining, see e.g., U.S. Pat. Nos. 2,929,603, 3,058,471 and 4,077,411. U.S. Pat. No. 4,077,411 for instance, describes an apparatus having a spring-loaded ring to secure the corneal tissue at its edges over a semi-spherical post. The introduction of a harmless liquid from below the tissue, through a conduit in the post, is said to provide a cushion to resist the downward pressure of the trephine blade.

In "Corneal Holder", Amer. J. Ophthalmol. 80(3) Part II:551–552 (1975), there is described a holder having a semi-spherical pedestal, a matching scleral sealing sleeve and a retaining ring. The sleeve retains the tissue on the pedestal at its scleral rim, and the ring locks the sleeve to the pedestal in a manner said to trap a cushion of air beneath the tissue, again to resist the downward pressure of the trephine blade.

It follows that throughout the typical functions involved from excision to implantation, the corneal tissue must frequently be handled a variety of times, e.g., by forceps, in order to place it in the storage vial upon excision, remove it and prepare it for microscopic evaluation, and place it and then orient it in a device or on a block for trephining. Each physical manipulation increases the chance of damage to the tissue, particularly at its edges and on its endothelial surface, and requires the patience, time and skill of a trained technician.

Throughout these functions, it would be highly desirable to be able to orient the corneal button with respect to its placement in the recipient eye. Kiely, et al, "Meridional Variations of Corneal Shape", Amer. J. Optom. Physiol. Optics, 61(10):619–626, 1984, for example, explains that the cornea in fact consists of four individual corneal meridians, each with its own radius of curvature. If the corneal tissue is transplanted into the recipient eye in a manner in which its radii are incompatible with those of the recipient eye, astigmatism can result. In order to limit this situation, surgeons currently must generally transplant corneal buttons in an unknown orientation in the eye, and then tighten and loosen the stitches holding the transplant, in an effort to hold the transplant in its desired configuration.

Currently practiced corneal tissue handling procedures do not generally allow the orientation of the corneal tissue or button. In fact, orientation is essentially lost from the moment the tissue is excised and placed to float freely in its storage medium.

Furthermore, it has been found that it may be desirable in some situations to prevent or lessen fluid absorption into the cut edges of the corneal tissue during storage. Undue absorption can lead to a swelling of the explant, thereby thickening it beyond use. One approach currently used in an attempt to avoid such thickening has been the development of modified storage media, as described in "Minnesota System Corneal Preservation" Lindstrom, et al, Brit. J. Ophthalmol., 70:47-54, 1986.

SUMMARY OF THE INVENTION

The present invention relates to a holder for corneal tissue, amenable for use in both a corneal storage system and a corneal cutting system with a minimal degree of physical manipulation of the tissue itself. The holder enables the tissue to be oriented in any desired position throughout storage, thereby enabling the surgeon to cut, orient and implant a predetermined portion, e.g, a corneal button, in a manner that limits astigmatism. The holder also facilitates the rapid and easy positioning and alignment of a cutting device in order to make a smooth, straight and concentric cut at the circumference of the predetermined portion of the corneal tissue. The holder also can be made to allow any desired degree of constriction of the rim of the tissue, so as to provide a barrier to fluid uptake in order to alleviate swelling of the tissue.

The present invention provides a corneal holder adapted to hold a corneal tissue while cutting a predetermined portion of the tissue, the holder comprising:

a base member having a first aperture of a size at least as large as the predetermined portion of the tissue, a cap member having a second aperture of a size at least as large as the predetermined portion of the tissue, and attachment means associated with the base member and the cap member for attaching the base member to the cap member, the base member and the cap member thereby cooperatively defining a compartment adapted to hold the predetermined portion in a retained relationship in alignment with the first and second apertures and defining a passageway through the first and second apertures configured to allow a cutting device to be passed through the passageway and into cutting contact with the circumference of the predetermined portion.

The present invention also provides a corneal storage system and a corneal cutting system comprising the corneal holder.

DETAILED DESCRIPTION OF THE INVENTION

Figure 1:
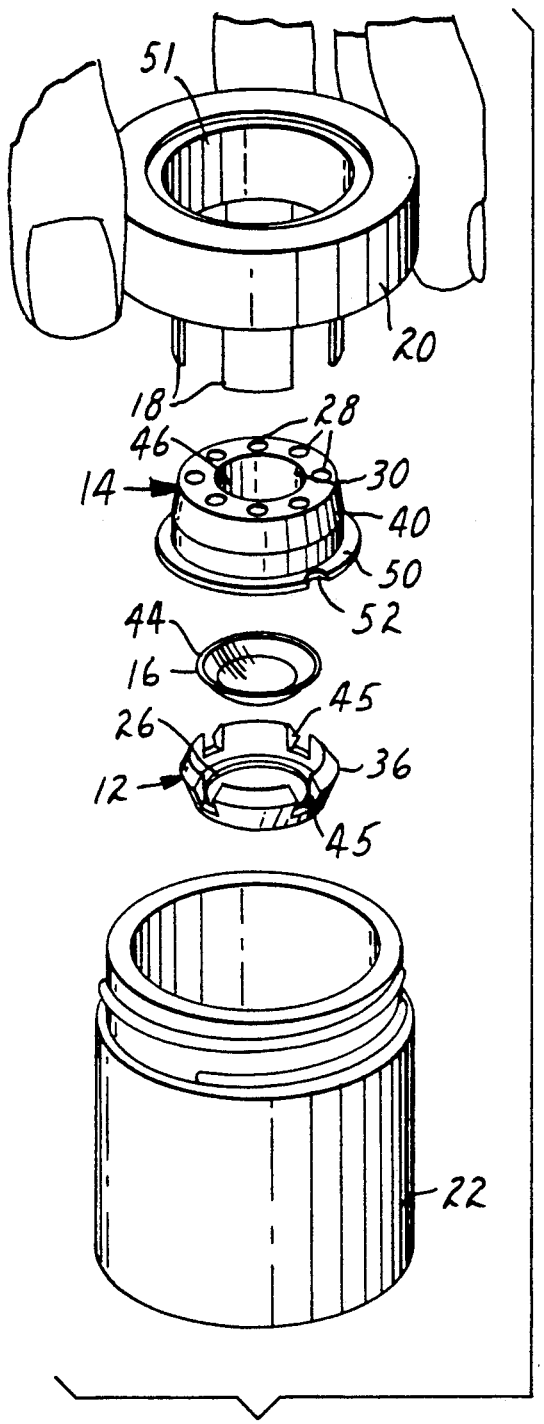
FIG. 1 is an exploded perspective view of one embodiment of a corneal storage system including a corneal holder of the invention.

The corneal holder of the present invention will be better understood by reference to the Drawing.

FIG. 1 is an exploded perspective view of one embodiment of a corneal storage system including a corneal holder of the invention. In FIG. 1 there is shown a disassembled corneal holder (10) comprising a base member (12) and a cap member (14), between which a corneal tissue (16) is shown for illustrative purposes. Holder (10) is designed so that it can be picked up and held using the jaws (18) of jar cover (20), and thereby transferred to storage jar (22) containing storage medium.

Base (12) has a first aperture (26) and base attachment means to enable secure attachment with cap (14). Cap (14) has a second aperture (30) capable of being aligned with the first aperture (26), and cap attachment means to enable secure attachment with base (12).

First aperture (26) and second aperture (30) are preferably both of substantially the same size, and of a size smaller than that of the tissue to be held but at least as large as the circumference of the predetermined portion, e.g., corneal button, to be cut.

Corneal tissue (16) as illustrated in FIG. 1 is excised from a donor eye by methods known in the art and is substantially circular in shape having a diameter, defined by its rim (44), that is at least as large as that of the first and second apertures, but that is generally not larger than the largest inner diameter defined by base sidewall (36). Typically tissue (16), if from a human donor, will be on the order of 15-20 mm in diameter, including a 2 to 3 mm rim of scleral tissue.

Corneal tissue is generally sufficiently rigid so that it will retain its natural curved shape, e.g., if placed with its epithelial side down in base (12), and can support its own weight at its point(s) of contact. As a result, the tissue will not typically fold over on itself or fall through first aperture (26), but will sit in a manner analogous to that of a watch glass covering an open hole.

Tissue (16) as shown, is positioned with its epithelial surface down over first aperture (26). Cover (14) is then attached to base (12) in a manner that defines a compartment that holds tissue (16) and that aligns first aperture (26) with second aperture (30) so as to define a passageway through the apertures that is configured to allow a cutting device to be passed through the passageway and into cutting contact with the circumference of the predetermined portion of tissue (16).

Tissue (16) is preferably held in its position in corneal holder (14) by pressure exerted at some point(s) on tissue (16). The pressure that retains tissue (16) can be applied at any of a variety of points. For instance, the inner diameter of base sidewall (36) might be such, with respect to the diameter of tissue (16) that tissue (16) is held by virtue of its own rigidity and the contact of its rim (44) against portions of base sidewall (36). Similarly, tissue (16) may be retained by the contact of its rim (44) with the underside of cap (14) such that tissue (16) is pressed against first aperture (26) with sufficient pressure to hold it in place.

Figure 4:
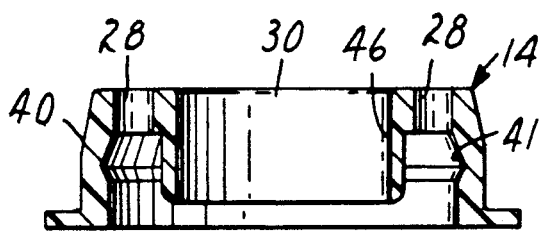
FIG. 4 is a cross-sectional view of the cap for the corneal holder of FIG. 1.
Figure 3:
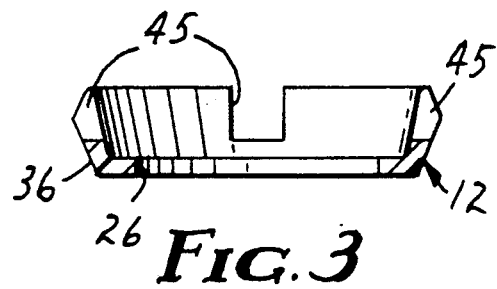
FIG. 3 is a cross-sectional view of the base of the corneal holder of FIG. 1.

In the embodiment illustrated in FIG. 1, tissue (16) is held by the presence of constricting means, which constricting means is formed in part by a cylindrical protrusion (46)(seen more clearly in the cross-sectional view of FIG. 4) extending downward from cap (14) from a point at or near second aperture (30). Cylindrical protrusion (46) exerts pressure upon the periphery of tissue (16), i.e., at points other than those within the predetermined portion, and causes slight constriction of tissue (16) between cylindrical protrusion (46) and first aperture (26) when cap (14) is attached to base (12).

The amount of constriction can be varied, e.g., by varying the dimensions of the constricting means, and will typically be in a range from the maximum that can be applied to tissue (16) without causing severe damage thereto, to the minimum that can be applied while still maintaining contact between tissue (16) and the constricting means.

Base attachment means and cap attachment means are mutually compatible so as to enable simple and secure attachment of base (12) and cap (14). Examples of suitable attachment means include pressure-, friction- or interlocking- type arrangements such as snap-fit and screw-fit arrangements.

A preferred attachment means is a snap-fit arrangement wherein the sidewalls of one holder member i.e., the base or the cap, are recessed, grooved, stepped or otherwise configured to retain an oppositely configured mating partner, upon the application of a slight engaging force or motion.

Shown in FIG. 1 for instance, is a snap-fit arrangement in which base sidewall (36) extends upwardly and radially outward at the periphery of base (12) on an axis that is at an angle of approximately 80° with the plane of the bottom of base (12). The inner major surface of base sidewall (36) is substantially flat, and the outer major surface is angled first radially outward at an angle of approximately 67.5° from the plane of the bottom of base (12) to a distance of approximately one-half the height of the inner surface, and then radially inward to provide a rounded lead-in guide for the inner major surface of cap sidewall (40).

Cap sidewall (40) extends downwardly from the top of cap (14) and has an inner major surface that contains a circumferential groove (41) (seen more clearly in the cross-sectional view of FIG. 4) of a dimension capable of receiving and retaining the outermost portion of base sidewall (36).

Preferably base sidewall (36) has a plurality of radially located compression grooves (45), to enable base sidewall (36) to be slightly compressed radially inward during engagement with cap (14) and to expand again to its normal shape once within the cap, thereby locking base sidewall (36) into cover sidewall (40).

In the embodiment illustrated in FIG. 1, holder and jar cover engagement means are also provided, in order to allow jar cover (20) to pick up and transfer holder (10), e.g., to storage jar (22). These engagement means can be any means that allow holder (10) to be picked up in a simple, rapid, releasable and aseptic manner. Suitable engagement means include pressure-, friction- or inter-locking type arrangements.

Shown in FIG. 1 is a simple pressure-type arrangement wherein jar cover (20) is equipped with holder engagement means in the form of a plurality of radially located opposing resilient jaws (18) extending downwardly from jar cover (20). As the jar cover engagement means, the outer major surface of cap sidewall (40) is tapered radially inward as it approaches the top of cap (14) in order to provide a lead-in for grasping by jaws (18) of jar cover (20). Jaws (18) are expanded slightly during engagement with holder (10), in order to snugly hold holder (10) therein.

Holder (10) preferably also includes holder release means for removing holder (10) from secure engagement with jar cover (20). As shown in FIG. 1 for instance, cap (14) is provided with a flange (50) extending outwardly from the bottom of cap sidewall (40). Flange (50) can be held or secured, e.g., by the tip of a finger or instrument, while jar cover (20) is held and pulled away from holder (10), thereby releasing holder (10) from the grasp of jaws (18).

Flange (50) preferably performs an additional function in that it acts as a barrier to stop the downward movement of jaws (18). Flange (50) also helps to insure complete attachment of cap (14) with base (12) by virture of the downward pressure of jaws (18) on flange (50), thereby forcing cap (14) down until flange (50) rests uniformly on a preferably flat work-station surface (not shown).

Holder (10) preferably also includes orientation means, e.g., notch (52) in flange (50) that enables tissue (16) to be placed in holder (10) in a known radial orientation.

Also associated with the holder shown in the embodiment illustrated in FIG. 1 are port means, shown as a plurality of generally circular and equally spaced holes (28) through the top of cap (14), to allow fluid such as storage medium to have continuous access into the compartment defined by base (12) and cap (14) in order to bathe the edges of the tissue held therein.

Base (12) and cap (14) can be made out of any suitable material that is sufficiently strong, inert, resilient and compatible for such use. Preferred materials are plastics such as polypropylene. Both members can be manufactured, e.g., as one-part injection molded pieces, by methods well known in the pertinent art.

As shown in FIG. 1, jar cover (20) includes an optically clear viewing port (51). Viewing port (51) is indented into jar cover (20) in order to allow visual inspection of the tissue, e.g., as described in "Wide Field Specular Microscopy of Excised Donor Corneas", C. W. Roberts et al., Arch. Ophthalmol. 99:881–883 (1981), and "Examination and Photography of Donor Corneal Endothelium, W. M. Bourne, Arch. Ophthalmol. 94:1799–1800 (1976). In addition to the holder engagement means described earlier, jar cover (20) also preferably includes means for releasably securing jar cover (20) to storage jar (22), preferably a screw-type or snap-fit arrangement wherein jar cover (20) is screwed or snapped onto storage jar (22).

Jar cover (20) and storage jar (22) can be made by methods known in the art of any of a variety of materials known for such uses. Typically, jar cover (20) will be molded plastic, having optically clear plastic or glass as viewing port (51) and resilient, e.g., plastic, jaws. Jar (22) will typically be made of a clear or translucent glass or plastic material, by manufacturing techniques well known in the art.

The following procedure is typically performed in order to use the corneal storage system shown in FIG. 1.

Under asceptic conditions, a cornea is excised from a donor eye to provide tissue (16), which is transferred by forceps to rest in a known radial orientation with respect to notch (52), epithelial side down, within base (12). Cap member (14) is picked up and oriented above base (12) so as to approximately align first aperture (26) and second aperture (30). Cap (14) and base (12) are then securely attached, e.g., by a snap-fit motion, so that tissue (16) is held between the two, such that both major surfaces of the predetermined portion from which the corneal implant is to be cut are exposed through the first and second apertures, and such that there is slight pressure constricting tissue (16) between cylindrical protrusion (46) and base (12) at points peripheral to the predetermined portion. Both major surfaces of the predetermined portion, as well as the rim of the tissue and the surfaces peripheral to the points of constriction, are thereby accessible to storage medium when placed in storage jar (22). Jar cover (20) is then grasped and brought into a position whereby jaws (18) are brought down onto holder (10) until jaws (18) are stopped by flange (50), thereby releasably securing holder (10) to jar cover (20).

The resultant jar cover-holder assembly is transferred to storage jar (22), and jar cover (20) is screwed onto storage jar (22). Storage jar (22) preferably contains a sufficient amount of storage medium to completely submerge tissue (16) when storage jar (22) is stored in its usual inverted position.

Preferably fluid of the viscosity of storage media will be able to contact both major surfaces of tissue (16) i.e., through base aperture (26) and cover aperture (30), and will also be able to contact the edges of tissue (16), while holder (10) is held within storage jar (22).

Figure 2:
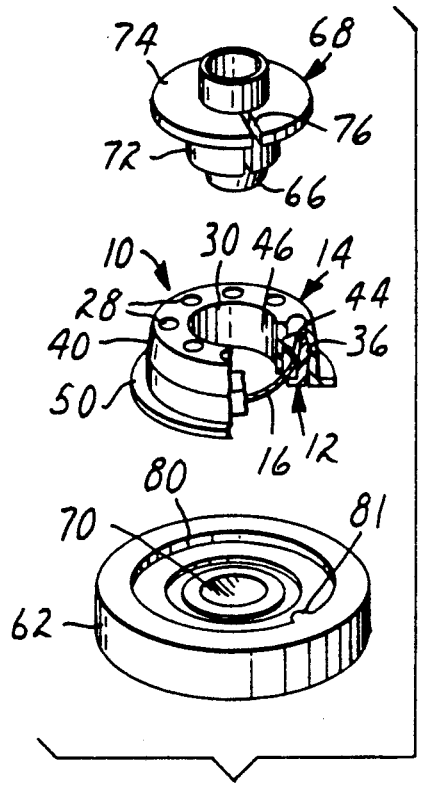
FIG. 2 is an exploded perspective view of an assembled corneal holder of FIG. 1 in a corneal cutting system.

Turning now to FIG. 2, there is shown a partially exploded perspective view of one embodiment of a corneal cutting system for use with the holder of the present invention. Shown is: assembled holder (10) containing tissue (16); base means, e.g., trephine block (62); and a blade assembly comprising a cutting device, e.g., trephine blade (66), and a blade holder (68).

In order to use the illustrated corneal cutting system, holder (10) is first placed such that flange (50) rests in a central location on block (62). Block (62) has a raised rim (80) that defines an inner diameter on the surface of block (62) that is slightly larger than the diameter of flange (50), such that flange (50) fits within the raised rim, in a substantially radially immovable position.

As shown in FIG. 2, the inner surface of rim (80) has an oppositely configured protrusion (81) to mate with notch (52) such that holder (10) can be placed on block (62) in an orientated and secure position. The surface of block (62) that faces holder (10) can have additional features, e.g., it can be concentrically grooved or otherwise formed, in order to provide any desired contour for use as a cutting surface.

When holder (10) sits properly on block (62), first aperture (26) is properly aligned with a semispherical indentation (70) in the center of block (62) that preferably has a diameter at least as large as the predetermined portion to be cut and a radius of curvature substantially the same as tissue (16).

Indentation (70) can be of any desired diameter or configuration, e.g., semicircular, angular or the like. See, e.g., "A New Punch for Corneal Transplantation", D. M. Lieberman, Amer. J. Ophthalmol. 83:419–420 (1977), wherein it is described that the angle and cleanness of the edges of a button cut out of a corneal tissue appears to be dependent in part on the diameter and/or configuration of the indentation in the trephining block.

A blade assembly is then set into the top of holder (10). The blade assembly shown in FIG. 2 has a blade holder (68) and, as the cutting device, blade (66). Blade holder (68) is typically a one-part molded piece of a sufficiently strong, inert, resilient and compatible material such as the materials used to make holder (10), having a cylindrical sleeve (72) and an outwardly extending sleeve flange (74). Blade holder (68) preferably has one or more expansion grooves (76) through sleeve (72) and sleeve flange (74) that allows blade holder (68) to be radially expanded an amount sufficient to accept and retain blade (66) therein. Expansion groove (76) can be used to radially orient the predetermined portion of tissue as well, by directing it towards the holder orientation means during cutting. Blade holder (68) has an inner diameter and resilience capable of then snugly retaining blade (66).

When blade (66) is held in blade holder (68) sleeve (72) defines an outer diameter slightly smaller than the inner diameter of cylindrical protrusion (46) of cap (14), such that sleeve (72) can be inserted within cylindrical protrusion (46) in a mating relationship whereby sleeve (72) is retained in a substantially radially immovable position.

Sleeve (72) has a length substantially the same as that of cylindrical protrusion (46). Although shown exposed below sleeve (72), blade (66) is initially oriented in sleeve (72) such that cutting edge (78) does not protrude below sleeve (72).

The cutting device will typically be a cylindrical metal trephine blade having a cutting edge that defines the desired diameter of a corneal button, and will typically be used to cut entirely through the circumference of the predetermined portion, although variations, e.g., on the size, dimensions and depth of the cut, are well known in the pertinent art.

Sleeve flange (74) provides an easy means for grasping blade holder (68) and is configured to rest on the top surface of holder (10) in order to place sleeve (72) and blade (66) within cylindrical protrusion (46). Cylindrical protrusion (46) therefore serves as a guide for sleeve (72) and, in turn, for blade (66), in order to allow blade (66) to be brought into proper cutting contact with the predetermined portion of tissue (16).

The corneal cutting system is then placed in an appropriate corneal punch mechanism (not shown) that forces blade (66) down through sleeve (72) such that the cutting edge of blade (66) proceeds into and through tissue (16) with a motion and force sufficient to cleanly cut a corneal button having the diameter of the cutting edge of blade (66).

The corneal button frequently remains within blade (66) until a drop of sterile fluid, e.g., storage medium is placed from above into the inner circumference of blade (66). The weight of the fluid is generally sufficient to cause the button to gently drop from blade (66), e.g., onto block (62).

The dimensions of corneal holder (10) may be varied in a manner commensurate with the size of tissue to be held, e.g., to accomodate tissue from different animal sources.

What is claimed is:

1. A corneal holder adapted to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, attachment means associated with said base member and said cap member for attaching said base member to said cap member, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion, and engagement means for releasably engaging said holder to a jar cover wherein said engagement means comprises a cap sidewall tapered radially inward as it approaches the top of said cap in order to provide a lead-in for jaws of a jar cover.

2. A corneal holder adapted to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, attachment means associated with said base member and said cap member for attaching said base member to said cap member, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion, and release means for removing said holder from releasable engagement with a jar cover wherein said release means comprises a flange extending outwardly from the bottom of said cap.

3. A corneal holder adapted to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, attachment means associated with said base member and said cap member for attaching said base member to said cap member, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion, and orientation means for holding said tissue in a known radial orientation.

4. A corneal holder according to claim 3 wherein said orientation means comprises a notch in said cap.

5. A corneal storage system comprising:
(a) a corneal holder adapted to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, and attachment means associated with said base member and said cap member for attaching said base member to said cap member, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion, (b) a storage jar, and
(c) a jar cover comprising means for releasably engaging said corneal holder and means for releasably securing said jar cover to said storage jar, whereby said holder can be picked up and held by said jar cover and transferred to said storage jar.

6. A corneal cutting system comprising
(a) a corneal holder adapted to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, and attachment means associated with said base member and said cap member for attaching said base member to said cap member, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion, (b) a base means capable of providing a base for said corneal holder, and
(c) a cutting device capable of being passed through the passageway of said corneal holder and into cutting contact with said circumference of said predetermined portion, whereby said holder can be placed on said base means, where said cutting device can be brought into said cutting contact with said circumference.

7. A corneal storage system comprising:
(a) a corneal holder adapted to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, and attachment means associated with said base member and said cap member for attaching said base member to said cap member, said base member and said cap member thereby cooperatively defining a compartment adapted to hold the predetermined portion in substantially its original form and in a retained relationship in alignment with said first and second apertures and defining a passageway through said first and second apertures configured to allow a cutting device to be passed through said passageway and into cutting contact with the circumference of said predetermined portion, (b) a storage jar, and (c) a jar cover comprising means for releasably engaging said corneal holder and means for releasably securing said jar cover to said storage jar, whereby said holder can be picked up and held by said jar cover and transferred to said storage jar, said engagement means comprising a plurality of radially located opposing resilient jaws extending downwardly from said jar cover, and a cap sidewall tapered inward as it approaches the top of said holder for grasping by said jaws.

8. A corneal holder adapted to be held by a jar cover, and to hold a corneal tissue while cutting a predetermined portion of said tissue, said holder comprising:

a base member having a first aperture of a size at least as large as said predetermined portion of said tissue, a cap member having a second aperture of a size at least as large as said predetermined portion of said tissue, attachment means associated with said base member and said cap member for attaching said base member to said cap member, and engagement means for releasably engaging said holder to a jar cover wherein said engagement means comprises a cap sidewall tapered radially inward as it approaches the top of said cap in order to provide a lead-in for jaws of a jar cover, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion.

9. A corneal cutting system comprising (a) a corneal holder comprising:

a base member having a first aperture of a size at least as large as said predetermined portion of said tissue, a cap member having a second aperture of a size at least as large as said predetermined portion of said tissue, and attachment means associated with said base member and said cap member for attaching said base member to said cap member, said base member and said cap member thereby cooperatively defining a compartment adapted to hold the predetermined portion in substantially its original shape and in a retained relationship in alignment with said first and second apertures and defining a passageway through said first and second apertures configured to allow a cutting device to be passed through said passageway and into cutting contact with the circumference of said predetermined portion, (b) a base means capable of providing a base for said corneal holder, and (c) a cutting device capable of being passed through the passageway of said corneal holder and into cutting contact with said circumference of said predetermined portion, whereby said holder can be placed on said base means, where said cutting device can be brought into said cutting contact with said circumference.

* * * * *